(12) United States Patent
Itu et al.

(10) Patent No.: US 11,931,195 B2
(45) Date of Patent: Mar. 19, 2024

(54) ASSESSMENT OF CORONARY ARTERY CALCIFICATION IN ANGIOGRAPHIC IMAGES

(71) Applicant: Siemens Healthineers AG, Forchheim (DE)

(72) Inventors: Lucian Mihai Itu, Brasov (RO); Diana Ioana Stoian, Brasov (RO); Tiziano Passerini, Plainsboro, NJ (US); Puneet Sharma, Princeton Junction, NJ (US)

(73) Assignee: Siemens Healthineers AG, Forchheim (DE)

(*) Notice: Subject to any disclaimer, the term of this patent is extended or adjusted under 35 U.S.C. 154(b) by 166 days.

(21) Appl. No.: 17/602,820

(22) PCT Filed: Jul. 22, 2019

(86) PCT No.: PCT/IB2019/000792
§ 371 (c)(1),
(2) Date: Oct. 11, 2021

(87) PCT Pub. No.: WO2021/014181
PCT Pub. Date: Jan. 28, 2021

(65) Prior Publication Data
US 2022/0151580 A1 May 19, 2022

(51) Int. Cl.
*G16H 50/20* (2018.01)
*A61B 6/00* (2006.01)
*G06T 7/00* (2017.01)

(52) U.S. Cl.
CPC .............. *A61B 6/504* (2013.01); *A61B 6/487* (2013.01); *G06T 7/0012* (2013.01); *G16H 50/20* (2018.01);
(Continued)

(58) Field of Classification Search
None
See application file for complete search history.

(56) References Cited

U.S. PATENT DOCUMENTS 7,689,017 B2 * 3/2010 Karl ...................... G06T 11/005
382/128
7,801,347 B2 * 9/2010 Wilson ............... A61B 5/02007
382/128
(Continued)

FOREIGN PATENT DOCUMENTS

CN 103337096 A 10/2013
CN 106447645 A 2/2017
(Continued)

OTHER PUBLICATIONS

Liu et al., "Current understanding of coronary artery calcification", Journal of Geriatric Cardiology, 2015, vol. 12, pp. 668-675.
(Continued)

*Primary Examiner* — Nancy Bitar

(57) ABSTRACT

Systems and methods are provided for training an artificial intelligence model for detecting calcified portions of a vessel in an input medical image. One or more first medical images of a vessel in a first modality and one or more second medical image of the vessel in a second modality are received. Calcified portions of the vessel are detected in the one or more first medical images, The artificial intelligence model is trained for detecting calcified portions of the vessel in the input medical image in the second modality based on the one or more second medical images and the detected calcified portions of the vessel detected in the one or more first medical images.

20 Claims, 11 Drawing Sheets

(52) U.S. Cl.
CPC ............... *G06T 2207/10081* (2013.01); *G06T 2207/10121* (2013.01); *G06T 2207/30101* (2013.01)

(56) References Cited

U.S. PATENT DOCUMENTS

| | | | |
|---|---|---|---|
| 8,031,927 B2 * | 10/2011 | Karl | ............... G06T 11/008 382/254 |
| 9,767,557 B1 | 9/2017 | Gulsun et al. | |
| 2011/0224542 A1 | 9/2011 | Mittal et al. | |
| 2018/0008222 A1 | 1/2018 | Chen et al. | |
| 2018/0055471 A1 * | 3/2018 | Redel | ............... G06T 11/003 |
| 2019/0051002 A1 | 2/2019 | Auvray et al. | |
| 2019/0054002 A1 * | 2/2019 | Yoon | ............... A61Q 19/10 |

FOREIGN PATENT DOCUMENTS

| | | |
|---|---|---|
| CN | 106570848 A | 4/2017 |
| CN | 109288536 A | 2/2019 |

OTHER PUBLICATIONS

Mehanna et al., Volumetric Characterization of Human Coronary Calcification by Frequency Domain Optical Coherence Tomography, Circ J., 2013, vol. 77(9), pp. 2334-2340.

Shimony et al., "Incidence, Risk Factors, Management and Outcomes of Coronary Artery Perforation During Percutaneous Coronary Intervention", Am J Cardiol, 2009, vol. 104, pp. 1674-1677.

Madhavan et al., "Coronary Artery Calcification Pathogenesis and Prognostic Implications", Journal of the American College of Cardiology, 2014, vol. 63(17), pp. 1703-1714.

Mintz, "Intravascular Imaging of Coronary Calcification and its Clinical Implications", JACC, 2015, vol. 8, pp. 461-471.

Jing et al., "Neural Style Transfer: A Review", https://arxiv.org/pdf/1705.04058.pdf, 2018.

Green et al., "Angiographic Views Used for Percutaneous Coronary Interventions: A Three-Dimensional Analysis of Physician-Determined vs. Computergenerated Views", Catheterization and Cardiovascular Interventions, 2005, vol. 64, pp. 451-459.

Cimen et al., "Reconstruction of Coronary Arteries from X-ray Angiography: A Review.", Medical Image Analysis, 2016, vol. 32, pp. 46-68.

9 International Search Report dated Mar. 9, 2020 in International Patent Application No. PCT/IB2019/000792.

* cited by examiner

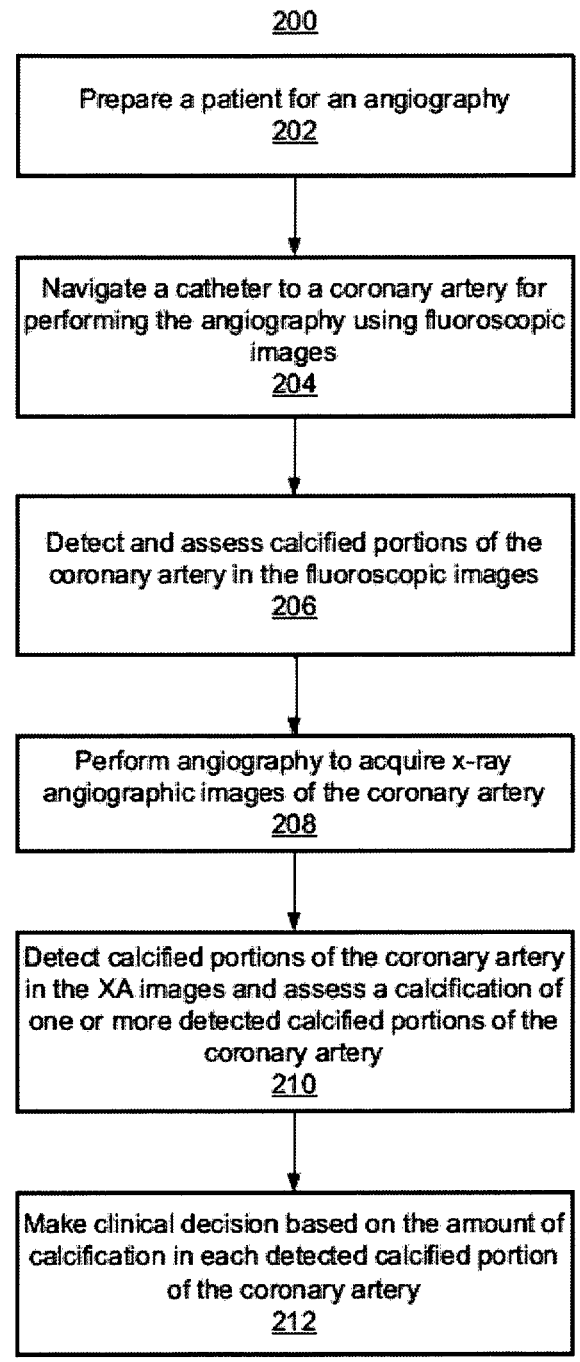

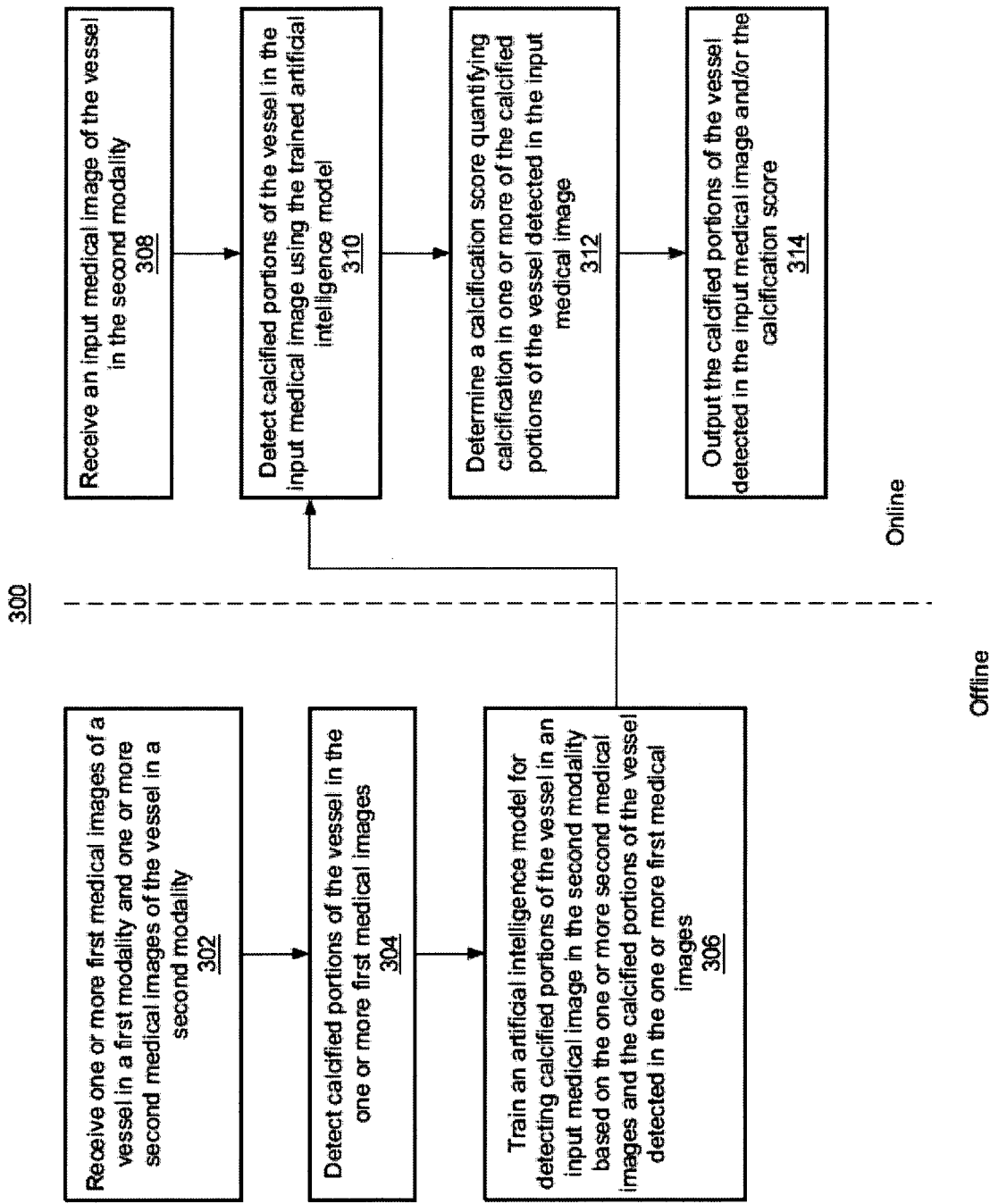

ASSESSMENT OF CORONARY ARTERY CALCIFICATION IN ANGIOGRAPHIC IMAGES

CROSS REFERENCE TO RELATED APPLICATIONS

This application is a national phase filing under 35 U.S.C. § 371 of International Patent Application No. PCT/IB2019/000792, filed Jul. 22, 2019, which is incorporated herein by reference in its entirety.

TECHNICAL FIELD

The present invention relates generally to the assessment of coronary artery calcification in angiographic images, and more particularly to training a machine learning model for assessing coronary artery calcification in angiographic images.

BACKGROUND

Coronary artery disease (CAD) is the narrowing of the coronary arteries due to the buildup of plaque, thereby causing blood flow to the heart to be restricted. Significant challenges arise in treating CAD where the plaque is calcified plaque. Specifically, treatment of CAD resulting from calcified plaque is associated with a higher rate of complications and a lower rate of success when compared to treatment of CAD resulting from non-calcified plaque (e.g., soft, fatty plaque such as cholesterol). For example, one treatment of CAD is percutaneous coronary intervention (PCI), which involves opening narrowed arteries using a stent or another device. However, it has been observed that PCI for treating calcified plaque in the coronary arteries often results in stent under-expansion, leading to an increase in the risk for acute medical events (e.g., restenosis), procedure time, radiation doses, and contrast agent dose.

Debulking technologies, such as rotational atherectomy, have been developed to ablate calcified plaque and facilitate delivery of coronary devices. Studies have shown that a planned rotational atherectomy strategy can result in a reduction in total procedure time, radiation dose, contrast agent dose, materials (e.g., pre-dilation balloon catheters), and medical costs. It is therefore important to objectively assess and quantify calcifications of the coronary arteries from routine angiographic images for clinical decision making, such as, e.g., determining whether or not to perform rotational atherectomy prior to PCI.

BRIEF SUMMARY OF THE INVENTION

In accordance with one or more embodiments, systems and methods are provided for training an artificial intelligence model for detecting calcified portions of a vessel in an input medical image. One or more first medical images of a vessel in a first modality and one or more second medical image of the vessel in a second modality are received. Calcified portions of the vessel are detected in the one or more first medical images. The artificial intelligence model is trained for detecting calcified portions of a vessel in the input medical image in the second modality based on the one or more second medical images and the calcified portions of the vessel detected in the one or more first medical images.

In accordance with one embodiment, the first modality is computed tomography, the second modality is x-ray angiography, and the one or more first medical images and the one or more second medical images are of a same patient. The artificial intelligence model may be trained by performing a co-registration between the one or more first medical images and the one or more second medical images, projecting the calcified portions detected in the one or more first medical images onto the one or more second medical images based on the co-registration, and training the artificial intelligence model based on the projected calcified portions of the vessel.

In accordance with one embodiment, the first modality is computed tomography, the second modality is x-ray angiography, and the one or more first medical images and the one or more second medical images are of different patients. The artificial intelligence model may be trained by generating one or more synthesized medical images of the vessel in the second modality based on the one or more first medical images using another artificial intelligence model and training the artificial intelligence model based on the one or more synthesized medical images of the vessel. The one or more synthesized medical images may each correspond to different acquisition angles. The other artificial intelligence model may be trained by grouping the one or more second medical images based on their acquisition angles, computing a two-dimensional projection of the one or more first medical images for each of the acquisition angles, and training the other artificial intelligence model based on the two-dimensional projection of the one or more first medical images for each of the acquisition angles and the grouped one or more second medical images.

In accordance with one embodiment, the first modality is an intravascular imaging modality, the second modality is x-ray angiography, and the one or more first medical images and the one or more second medical images are of different patients. The artificial intelligence model may be trained by computing longitudinal projections of the one or more first medical images for a plurality of angles, mapping the computed longitudinal projections of the one or more first medical images to a two-dimensional vessel tree, generating one or more synthesized medical images of the vessel in the second modality based on the two-dimensional vessel tree using another artificial intelligence model, and training the artificial intelligence model based on the one or more synthesized medical images. The one or more synthesized medical images may each correspond to one of the plurality of angles. The other artificial intelligence model may be trained by computing a longitudinal projection of the one or more first medical images for each of the plurality of angles, mapping the computed longitudinal projections to a particular two-dimensional vessel tree, and training the artificial intelligence model based on the particular two-dimensional vessel tree.

In accordance with one embodiment, the first modality is an intravascular imaging modality, the second modality is x-ray angiography, and the one or more first medical images and the one or more second medical images are of a same patient. The artificial intelligence model may be trained by performing a three-dimensional reconstruction of the vessel from the one or more second medical images, performing a co-registration between the one or more first medical images and the three-dimensional reconstruction of the vessel, projecting the calcified portions of the vessel detected in the one or more first medical images onto the three-dimensional reconstructions based on the co-registration, and training the artificial intelligence model based on the projected calcified portions of the vessel.

These and other advantages of the invention will be apparent to those of ordinary skill in the art by reference to the following detailed description and the accompanying drawings.

BRIEF DESCRIPTION OF THE DRAWINGS

FIG. 2 shows a high-level clinical workflow for facilitating clinical decision making for treating coronary artery disease;

FIG. 3 shows a high-level workflow for training and applying an artificial intelligence model for assessing a calcification of a coronary artery in an input medical image;

DETAILED DESCRIPTION

The present invention generally relates to the assessment of coronary artery calcification in angiographic images. Embodiments of the present invention are described herein to give a visual understanding of methods for the assessment of coronary artery calcification in angiographic images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while embodiments discussed herein may be discussed with respect to the assessment of coronary artery calcification in angiographic images, the present invention is not so limited. Embodiments of the present invention may be applied for assessing any type of plaque or other buildup in any type of structure (e.g., an anatomical structure or a non-anatomical structure) in any type of image.

Figure 1A:
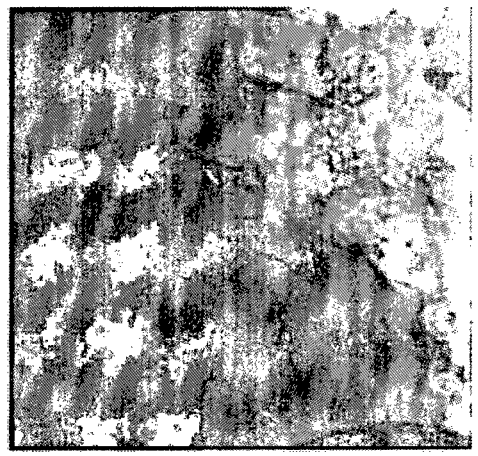
FIG. 1A shows an exemplary x-ray angiography image of coronary arteries.

FIG. 1A shows an exemplary x-ray angiography (XA) image 100 of a coronary artery. Portions of the coronary artery in XA image 100 are calcified. The calcified portions represent a buildup of calcium causing narrowing of the coronary artery. The calcified portions may be treated by percutaneous coronary intervention (PCI) to open the calcified portions of the coronary artery using a stent or other medical device. However, often times, treatment of calcified portions by PCI results in stent under-expansion due to the rigidity of the calcium in calcified portions.

Figure 1B:
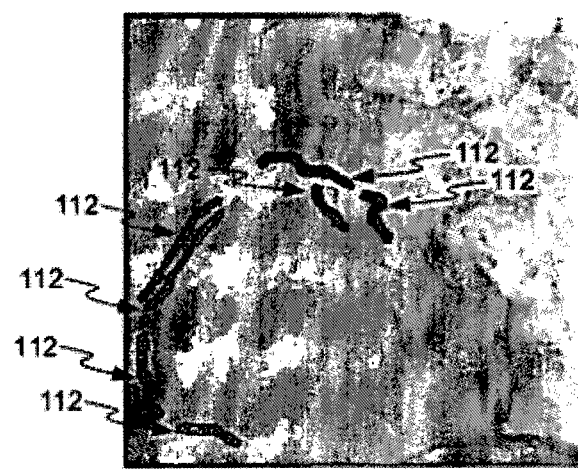
FIG. 1B shows an x-ray angiography image of coronary arteries overlaid with various detected calcified portions.

FIG. 1B shows an XA image 110 of a coronary artery having various calcified portions 112 overlaid thereon, in accordance with one or more embodiments. Embodiments of the invention provide for the detection and assessment of calcified portions 112 of the coronary artery in XA image 110. In one or more embodiments, artificial intelligence (AI) based approaches are described for automatically detecting calcified portions of a coronary artery in an XA image. The coronary artery may be assessed by determining a calcification score quantifying the calcification, e.g., in one or more of the detected calcified portions or in the XA image. Such embodiments may be incorporated into a clinical workflow to facilitate clinical decision making, e.g., for treating calcified portion 112. For example, by assessing calcified portion 112, it can be determined whether to perform a rotational atherectomy or other debulking technique prior to performing PCI, thereby avoiding stent under-expansion or complications of PCI and reducing total procedure time, radiation dose, contrast agent dose, materials, and costs.

FIG. 2 shows a high-level clinical workflow 200 for facilitating clinical decision making for treating CAD (or any other medical condition), in accordance with one or more embodiment.

At step 202, a patient is prepared for an angiography. For example, a clinician (or any other medical professional) may set up a vascular access point for accessing a coronary artery (or any other vessel of interest). The vascular access point may be any suitable access point, such as, e.g., the femoral artery, radial artery, or brachial artery.

At step 204, a catheter is navigated to the coronary artery for performing the angiography using fluoroscopic images for guidance. The navigation of the catheter to the coronary artery facilitates the dispersal of a contrast agent to the coronary artery for performing the angiography.

At step 206, calcified portions of the coronary artery are detected and assessed in the fluoroscopic images. The fluoroscopic images are acquired utilizing little or no contrast agent and, consequently, calcified portions of the coronary artery are not clearly visible in such fluoroscopic images. The assessment of the calcification of the coronary artery in the fluoroscopic images may be represented as a calcification score quantifying the calcification of the coronary artery in the fluoroscopic images. In one embodiment, the calcification of the coronary artery is assessed in the fluoroscopic images by applying a trained artificial intelligence model trained and applied according to workflow 300 of FIG. 3.

At step 208, the angiography is performed to acquire XA images of the coronary artery. For example, the XA images may be cine-angiographic images of the coronary artery. The angiography is performed using the contrast agent.

At step 210, calcified portions of the coronary artery are detected in the XA images and the calcification of specific calcified portions (e.g., lesions or other regions of interest) in the detected calcified portions is assessed. The XA images are acquired using the contrast agent and, as such, the calcified portions of the coronary artery are visible in the XA images to allow a mapping between the calcified portions and the coronary artery. The assessment of the calcification of the coronary artery in the XA images may be represented as a calcification score quantifying the calcification one or more calcified portions of the coronary artery detected in the XA images. In one embodiment, the calcification of one or more calcified portions of the coronary artery is detected and assessed in the XA images by applying a trained artificial intelligence model trained and applied according to workflow 300 of FIG. 3.

At step 212, a clinical decision is made based on the assessment of the calcification in each detected calcified portion of the coronary artery. For example, the clinical decision may be to perform a debulking technique, such as, e.g., rotational atherectomy, before performing PCI where the assessment of the calcification in a detected calcified portion of the coronary artery indicates high calcification. In another example, the clinical decision may be to perform PCI, without performing a debulking technique, on a detected calcified portion of the coronary artery if the assessment of the calcification in the detected calcified portion of the coronary artery indicates low calcification. Other clinical decisions are also contemplated.

FIG. 3 shows a high-level workflow 300 for training and applying an artificial intelligence model for assessing a calcification of a coronary artery in an input medical image, in accordance with one or more embodiments. Steps of workflow 300 may be performed by any suitable computing device, such as, e.g., computer 1402 of FIG. 14, unless otherwise noted. Blocks 302-306 show an offline or training stage for training an artificial intelligence model for detecting calcified portions of a vessel in an input medical image. Blocks 308-314 show an online or testing stage for applying the trained artificial intelligence model. In one or more embodiments, the trained artificial intelligence model may be applied in steps 206 and/or 210 of FIG. 2.

During an offline stage, at block 302, one or more first medical images of a vessel in a first modality and one or more second medical images of the vessel in a second modality are received. In one embodiment, the vessel is a coronary artery of the patient, but may be any vessel (e.g., carotid arteries, aorta, renal arteries, peripheral arteries, etc.). The first modality and the second modality may be of any suitable but different modalities, such as, e.g., computed tomography (CT) (e.g., coronary computed tomography angiography, CCTA), x-ray (e.g., XA), intravascular (IV) imaging such as, e.g., optical coherence tomography (OCT) and intravascular ultrasound (IVUS), or any other suitable modality. XA images may include, e.g., fluoroscopic images in which little or no contrast agent is applied or cine XA images where contrast agent is applied. In accordance with one or more embodiments, the one or more first medical images and the one or more second medical images may be of a same patient or of different patients (i.e., the first medical images and the second medical images are independent). The one or more first medical images and the one or more second medical images may be received from one or more medical imaging systems or by loading previously stored images of the patient acquired using the medical imaging systems.

At block 304, calcified portions of the vessel are detected in the one or more first medical images. The calcified portions of the vessel may be manually annotated in the first medical image by a clinician, or may be automatically or semi-automatically detected using any suitable approach. In one example, the calcified portions of the vessel may be detected using an artificial intelligence model trained based on annotated training data. In another example, the calcified portions of the vessel may be detected according to the method described in U.S. patent application Ser. No. 15/548,581, filed Aug. 3, 2017, or the method described in U.S. Pat. No. 9,767,557, filed Feb. 10, 2017, the disclosures of which are incorporated herein by reference in their entirety. The detected calcified portions of the vessel may be represented by one or more bounding boxes, segmentations, labeled or highlighted pixels in the one or more first medical images, or any other suitable form.

At block 306, an artificial intelligence model is trained to predict calcified portions of the vessel in an input medical image in the second modality based on the one or more second medical images and the detected calcified portions of the vessel detected in the one or more first medical images. The artificial intelligence model may be any suitable artificial intelligence model. For example, the artificial intelligence model may be a machine learning model such as, e.g., a neural network. In one embodiment, the artificial intelligence model may be trained according to method 500 of FIG. 5 where the one or more first medical images are CCTA images and the one or more second medical images are XA images of a same patient. In another embodiment, the artificial intelligence model may be trained according to method 600 of FIG. 6 where the one or more first medical images are CCTA images and the one or more second medical images are XA images of different patients. In another embodiment, the artificial intelligence model may be trained according to method 800 of FIG. 8 where the one or more first medical images are IV images (e.g., OCT or IVUS images) and the one or more second medical images are XA images of different patients. In another embodiment, the artificial intelligence model may be trained according to method 1100 of FIG. 11 where the one or more first medical images are IV images and the one or more second medical images are XA images of the same patient.

During an online stage, at block 308, an input medical image of the vessel in the second modality is received. The input medical image may be received directly from an image acquisition device used to acquire the input medical image. Alternatively, the input medical image may be received by loading a previously acquired medical image from a storage or memory of a computer system or receiving a medical image that has been transmitted from a remote computer system.

Figure 4:
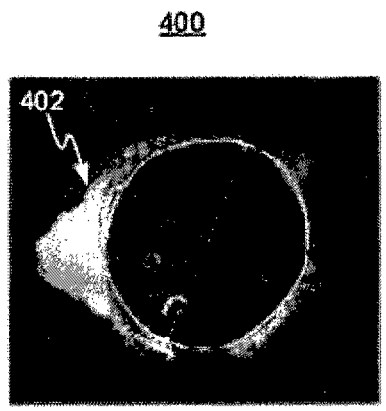
FIG. 4 shows an exemplary intravascular ultrasound image having detected calcified portions highlighted.

At block 310, calcified portions of the vessel are detected in the input medical image using the trained artificial intelligence model. The calcified portions of the vessel in the input medical image may be represented by one or more bounding boxes, segmentations, labeled or highlighted pixels in the input medical image, or any other suitable form. FIG. 4 shows an intravascular ultrasound (IVUS) image 400 having detected calcified portions 402 highlighted (e.g., by modifying the pixel intensity value).

At block 312, a calcification score for the input medical image is determined based on the detected calcified portions of the vessel detected in the input medical image. The calcification score represents a quantification of calcification detected in a region of interest of the input medical image. In one embodiment, the region of interest is the entire input medical image. In another embodiment, the region of interest is one or more of the detected calcified portions of the vessel. For example, the region of interest may be detected calcified portions associated with a particular branch, segment, or region of the coronary artery.

The calcification score may be computed using any suitable approach. In one embodiment, the calcification score is computed as the number of pixels that depicts calcification of the vessel in the region of interest. In another embodiment, the calcification score is computed as a sum of the intensity values for each pixel that depicts calcification of the vessel in the region of interest. The intensity values for each pixel that depicts calcification of the vessel in the region of interest may be normalized based on all pixels that depict the vessel in the input medical image, e.g., using a vesselness model. Other methods of determining the calcification score are also contemplated.

At block 314, the calcified portions of the vessel detected in the input medical image and/or the calcification score are output. For example, the calcified portions of the vessel detected in the input medical image and/or the calcification score can be output by displaying the calcified portions of the vessel detected in the input medical image and/or the calcification score on a display device of a computer system, storing the calcified portions of the vessel detected in the input medical image and/or the calcification score on a memory or storage of a computer system, or by transmitting the calcified portions of the vessel detected in the input medical image and/or the calcification score to a remote computer system. FIG. 1B shows an exemplary output of XA image 110 of a coronary artery having various calcified portions 112 overlaid thereon.

It should be understood that once the trained artificial intelligence model is trained in the training stage (blocks 302-306), the online stage (blocks 308-314) can be repeated for each newly received input medical image to assess calcification of a vessel in the newly received input medical images. For example, blocks 308-314 can be repeated for a second input medical image of the vessel.

In one embodiment, the artificial intelligence model can be trained to directly predict the calcification score quantifying the calcification in the input medical image during the training stage. In particular, during the training stage, a calcification score is determined quantifying calcification in a region of interest of the one or more first medical images. At block 306, the artificial intelligence model is trained to determine the calcification score in the input medical image based on the second medical image, the detected calcified portions of the vessel, and the calcification score. During the online stage, at block 310, the trained artificial intelligence model is used to directly determine the calcification score for the input medical image, without having to perform block 312.

Figure 5:
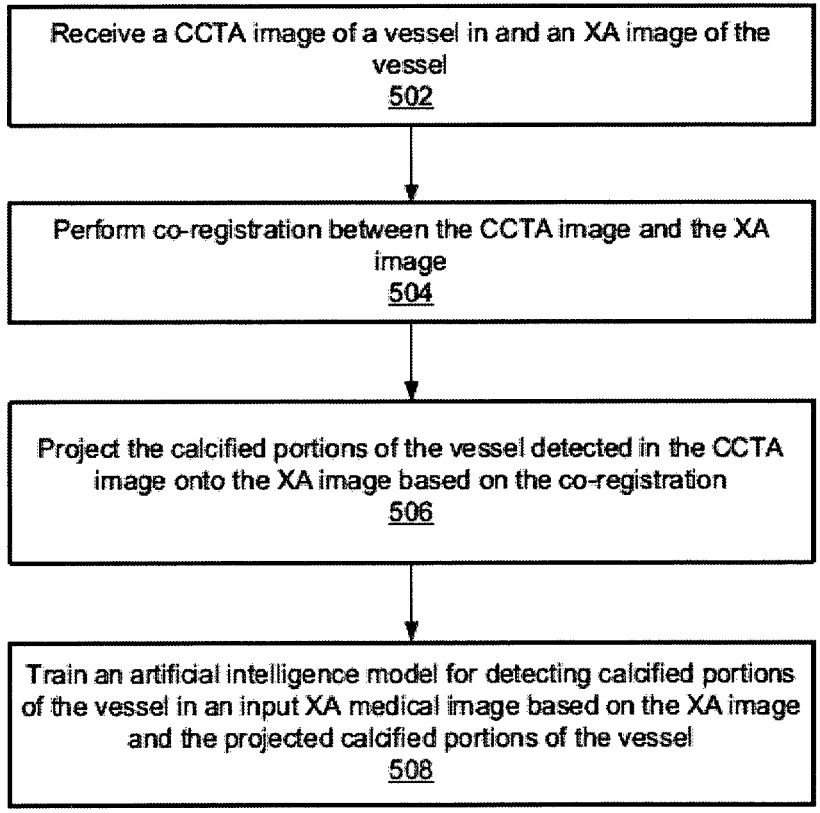
FIG. 5 shows a method for training an artificial intelligence model for detecting calcified portions of a vessel in an input x-ray angiography medical image based on a coronary computed tomography angiography image and an x-ray angiography image of a same patient.

FIG. 5 shows a method 500 for training an artificial intelligence model for detecting calcified portions of a vessel in an input XA medical image based on a CCTA and an XA image of a same patient, in accordance with one or more embodiments. Steps of method 500 may be performed by any suitable computing device, such as, e.g., computer 1402 of FIG. 14, unless otherwise noted. In one embodiment, the steps of method 500 are performed at block 306 of workflow 300 in FIG. 3 where the CCTA image corresponds to the first medical image in the first modality and the XA image corresponds to the second medical image in the second modality. It should be understood that while method 500 is described with respect to a CCTA image and an XA image, the images may be of any suitable modality.

At step 502, a CCTA image of a vessel (e.g., coronary artery) and an XA image of the vessel are received. The CCTA image and the XA image are of a same vessel of a same patient. The XA image may include a fluoroscopic image where little or no contrast agent is utilized or a cine XA image where a dose of contrast agent is utilized.

At step 504, co-registration is performed between the CCTA image and the XA image. The co-registration spatially aligns features of the CCTA image and the XA image to generate a composite image that defines a correspondence between pixels of the CCTA image and the XA image. The co-registration may be performed, e.g., manually, automatically, or semi-automatically. For example, the co-registration may be performed using image correspondence techniques using, e.g., markers or other features (e.g., bifurcations, stenoses, ostium, stents, etc.). Other (e.g., known) techniques for performing co-registration may also be applied.

At step 506, calcified portions of the vessel detected in the CCTA image (e.g., detected at step 304 of FIG. 3) are projected onto the XA image based on the co-registration. In particular, the pixels in the XA image that correspond to the pixels depicting the calcified portions of the vessel in the CCTA image are determined based on the co-registration (e.g., the composite image resulting from the co-registration). The projected calcified portions of the vessel in the XA image may be represented by one or more bounding boxes, segmentations, labeled or highlighted pixels in the XA image, or any other suitable form.

At step 508, an artificial intelligence model is trained for detecting calcified portions of the vessel in an input XA medical image based on the XA image and the projected calcified portions of the vessel. The artificial intelligence model may be any suitable artificial intelligence model, such as, e.g., a machine learning model. For example, the artificial intelligence model may be a convolutional neural network (e.g., U-net). It should be understood that the steps of method 500 may be performed for any number of pairs of CCTA and XA images (each of a same respective patient) to train the artificial intelligence model.

Figure 6:
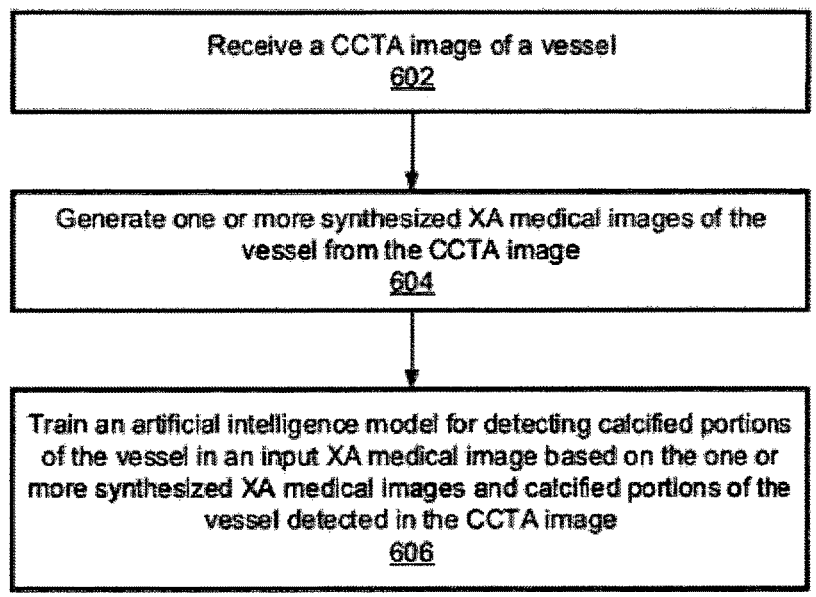
FIG. 6 shows a method for training an artificial intelligence model for detecting calcified portions of a vessel in an input x-ray angiography medical image based on a coronary computed tomography angiography image and an x-ray angiography image of different patients.

FIG. 6 shows a method 600 for training an artificial intelligence model for detecting calcified portions of a vessel in an input XA medical image based on a CCTA image and an XA image of different patients, in accordance with one or more embodiments. Steps of method 600 may be performed by any suitable computing device, such as, e.g., computer 1402 of FIG. 14, unless otherwise noted. In one embodiment, the steps of method 600 are performed at block 306 of workflow 300 in FIG. 3 where the CCTA image corresponds to the first medical image in the first modality and the XA image corresponds to the second medical image in the second modality. It should be understood that while method 600 is described with respect to a CCTA image and an XA image, the images may be of any suitable modality.

At step 602, a CCTA image of a vessel (e.g., coronary artery) and an XA image of the vessel are received. In one embodiment, the CCTA image and the XA image may be of different patients.

At step 604, one or more synthesized XA medical images of the vessel are generated from the CCTA image. In one embodiment, each of the one or more synthesized XA medical images correspond to an XA image acquired at a different acquisition angles. The locations of calcified portions of the vessel detected in the CCTA image (e.g., detected at block 304 of FIG. 3) correspond to locations in the one or more synthesized XA medical images since the one or more synthesized XA medical images are generated from the CCTA image.

The one or more synthesized XA medical images may be generated using any suitable approach. In one embodiment, the one or more synthesized XA medical images are generated using another trained artificial intelligence model trained using the CCTA image and the XA image. In one embodiment, the other artificial intelligence model is trained to generate the one or more synthesized XA medical images according to method 700 of FIG. 7.

At step 606, an artificial intelligence model is trained for detecting calcified portions of the vessel in an input XA medical image based on the one or more synthesized XA medical images and calcified portions of the vessel in the synthesized XA medical images (corresponding to the locations of the calcified portions detected in the CCTA image). The artificial intelligence model may be any suitable artificial intelligence model, such as, e.g., a machine learning model.

Figure 7:
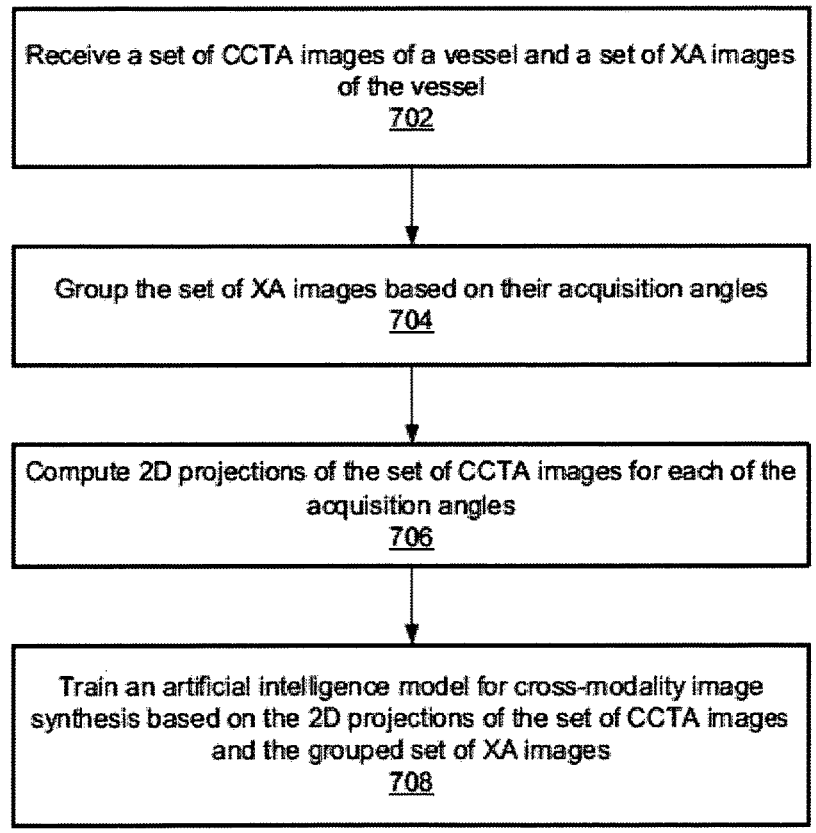
FIG. 7 shows a method for training an artificial intelligence model for generating one or more synthesized x-ray angiography medical images of a vessel from a coronary computed tomography angiography image.

FIG. 7 shows a method 700 for training an artificial intelligence model for generating one or more synthesized XA medical images of a vessel from a CCTA image, in accordance with one or more embodiments. Steps of method 700 may be performed by any suitable computing device, such as, e.g., computer 1402 of FIG. 14. In one embodiment, the trained artificial intelligence model trained according to method 700 may be applied in step 604 of FIG. 6 during an online stage. It should be understood that while method 700 is described with respect to a CCTA images and XA images, the images may be of any suitable modality.

At step 702, a set of CCTA images of a vessel and a set of XA images of the vessel are received. In one embodiment, the CCTA images are 3D CT volumes and the XA images include images acquired at different acquisition angles (e.g., primary and secondary acquisition angles). In one embodiment, the set of CCTA images and the set of XA images are of different patients.

At step 704, the set of XA images are grouped based on their acquisition angles. For example, XA images having similar (e.g., within a threshold amount) primary and secondary acquisition angles may be grouped together.

At step 706, 2D projections of the set of CCTA images are computed for each of the acquisition angles. The 2D projections may be parallel projections, perspective projections, etc. Accordingly, for each CCTA image of the set of CCTA images, a 2D CCTA projection is computed for each of the different acquisition angles.

At step 708, an artificial intelligence model is trained for cross-modality image synthesis based on the 2D projections of the set of CCTA images and the grouped set of XA images. The artificial intelligence model is trained to generate synthesized XA medical images for each of the acquisition angles from an input CCTA medical image. The artificial intelligence model may be any suitable artificial intelligence model (e.g., a machine learning model).

In one embodiment, the artificial intelligence model trained for cross-modality image synthesis is a generative adversarial network (GAN). The GAN comprises two modules in the form of deep networks: a generator for generating a synthesized XA image and a discriminator for distinguishing between a real image and the synthesized image. During the training stage, the generator generates one or more synthesized XA images from an input CCTA image. The discriminator receives as input the synthesized XA images generated by the generator and a real XA image and classifies one image as real and the other image as fake (synthesized). The generator and discriminator are simultaneously trained such that while the discriminator is improving in terms of fake image detection, the generator is improving in terms of producing realistic looking images capable of fooling the discriminator. Accordingly, the generator and discriminator are trained with adversarial loss to force the generator to learn the most meaningful features. During the online stage, the trained generator of the GAN is applied to generate one or more synthesized XA medical images from a CCTA image. The discriminator is only used during the training stage, and is not used during the online or inference stage. In one embodiment, the one or more synthesized XA medical images of the vessel is generated from CCTA image using a GAN as described in U.S. Pat. No. 9,760,807, entitled "Deep Image-to-Image Network Learning for Medical Image Analysis," filed Dec. 16, 2016, the disclosure of which is incorporated herein by reference in its entirety.

Figure 8:
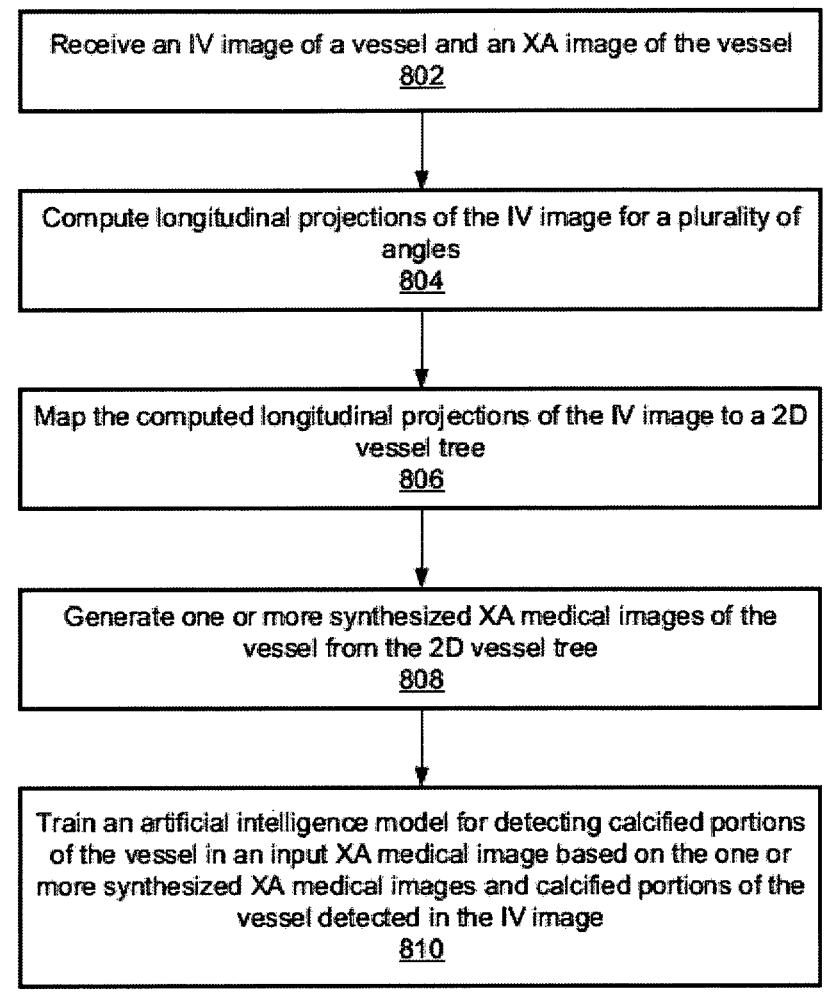
FIG. 8 shows a method for training an artificial intelligence model for detecting calcified portions of a vessel in an input x-ray angiography medical image based on an intravascular image and an x-ray angiography image of different patients.

FIG. 8 shows a method 800 for training an artificial intelligence model for detecting calcified portions of a vessel in an input XA medical image based on an intravascular (IV) image and an XA image of different patients, in accordance with one or more embodiments. Steps of method 800 may be performed by any suitable computing device, such as, e.g., computer 1402 of FIG. 14, unless otherwise noted. In one embodiment, the steps of method 800 are performed at block 306 of workflow 300 in FIG. 3 where the IV image corresponds to the first medical image in the first modality and the XA image corresponds to the second medical image in the second modality. It should be understood that while method 800 is described with respect to a IV images and XA images, the images may be of any suitable modality.

At step 802, an IV image of a vessel (e.g., coronary artery) and an XA image of the vessel are received. The IV image of the vessel may be of any IV modality, such as, e.g., OCT or IVUS. In one embodiment, the IV image and the XA image are of different patients.

Figure 9:
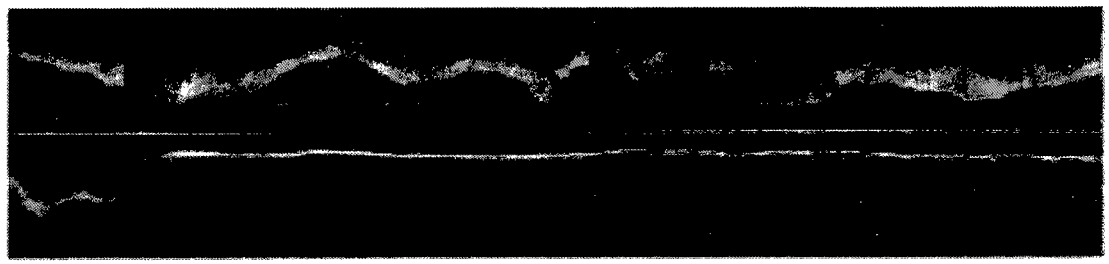
FIG. 9 shows an exemplary longitudinal projection of an intravascular image.

At step 804, longitudinal projections of the IV image are computed for a plurality of angles. In general, the IV image comprises a set of 2D images along a centerline of the vessel (i.e., cross-sectional views along the centerline). The 2D images form a 3D volume. The longitudinal projections may be obtained by projecting this 3D volume perpendicular to the centerline. Different longitudinal projections may be obtained corresponding to different acquisition angles. FIG. 9 shows an exemplary longitudinal projection 900.

At step 806, the computed longitudinal projections of the IV image are mapped to a 2D vessel tree. The 2D vessel tree may be a binary vessel tree, where pixels set to 0 represent background and pixels set to 1 represent vessels. In one embodiment, the computed longitudinal projections of the IV image are mapped to the 2D vessel tree by mapping the computed longitudinal projections of the IV image to a 3D vessel tree, and then projecting the 3D vessel tree to a 2D space to provide the 2D vessel tree. In another embodiment, the computed longitudinal projections of the IV image are mapped to the 2D vessel tree by directly mapping the longitudinal projections of the IV image to the 2D vessel tree. The computed longitudinal projections of the IV image may be mapped to the 2D vessel tree by mapping the computed longitudinal projections of the IV image to an atlas representing a generic vessel (e.g., generic coronary tree). The longitudinal projections may be mapped to any region of the coronary atlas. The mapping of the computed longitudinal projections of the IV image to the 2D vessel tree will add curvature to vessels providing for realistic coronary angiography generation.

At step 808, one or more synthesized XA medical images of the vessel are generated from the 2D vessel tree. In one embodiment, each of the one or more synthesized XA medical images correspond to one of the plurality of angles that the computed longitudinal projections are computed for. The locations of calcified portions of the vessel detected in the IV image (e.g., detected at block 304 of FIG. 3) correspond to locations in the one or more synthesized XA medical images since the one or more synthesized XA, medical images are generated from computed longitudinal projections of the IV image.

The one or more synthesized XA medical images may be generated using any suitable approach. In one embodiment, the one or more synthesized XA medical images are generated using another trained artificial intelligence model trained using the IV image and the XA image. In one embodiment, the other artificial intelligence model is trained to generate the one or more synthesized XA medical images according to method 1000 of FIG. 10.

At step 810, an artificial intelligence model is trained for detecting calcified portions of the vessel in an input XA medical image based on the one or more synthesized XA medical images and calcified portions of the vessel detected in the CCTA image. The artificial intelligence model may be any suitable artificial intelligence model, such as, e.g., a machine learning model.

Figure 10:
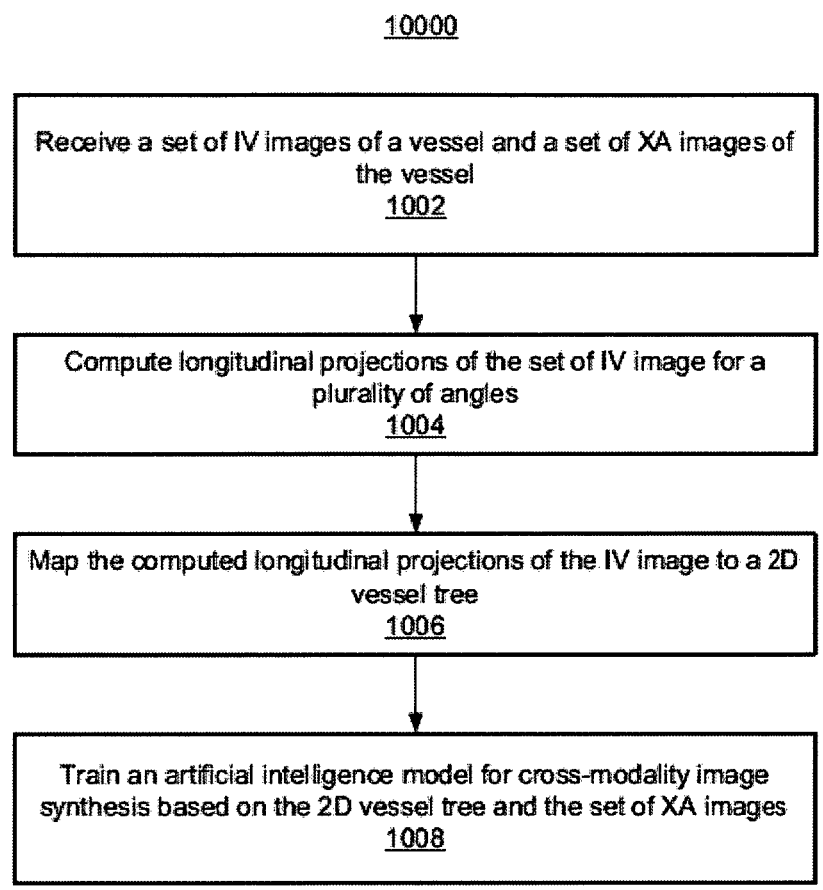
FIG. 10 shows method for training an artificial intelligence model for generating one or more synthesized x-ray angiography medical images of a vessel from a 2D vessel tree image.

FIG. 10 shows a method 1000 for training an artificial intelligence model for generating one or more synthesized XA medical images of a vessel from a 2D vessel tree image, in accordance with one or more embodiments. Steps of method 1000 may be performed by any suitable computing device, such as, e.g., computer 1402 of FIG. 14. In one embodiment, the trained artificial intelligence model trained according to method 1000 may be applied in step 808 of FIG. 8 during an online stage. It should be understood that while method 1000 is described with respect to a IV images and XA images, the images may be of any suitable modality.

At step 1002, a set of IV images of a vessel and a set of XA images of the vessel are received. In one embodiment, the set of IV images and the set of XA images are of different patients.

At step 1004, longitudinal projections of the set of IV images are computed for a plurality of angles. Accordingly, for each IV image of the set of IV images, longitudinal projections are computed for each of the plurality of angles.

At step 1006, the computed longitudinal projections of the IV image are mapped to a 2D vessel tree.

At step 1008, an artificial intelligence model is trained for cross-modality image synthesis based on the 2D vessel tree and the set of XA images. The artificial intelligence model is trained to generate synthesized XA medical images for each of the plurality of angles from an input IV medical image. The artificial intelligence model may be any suitable artificial intelligence model (e.g., a machine learning model). In one embodiment, the artificial intelligence model is a GAN.

Figure 11:
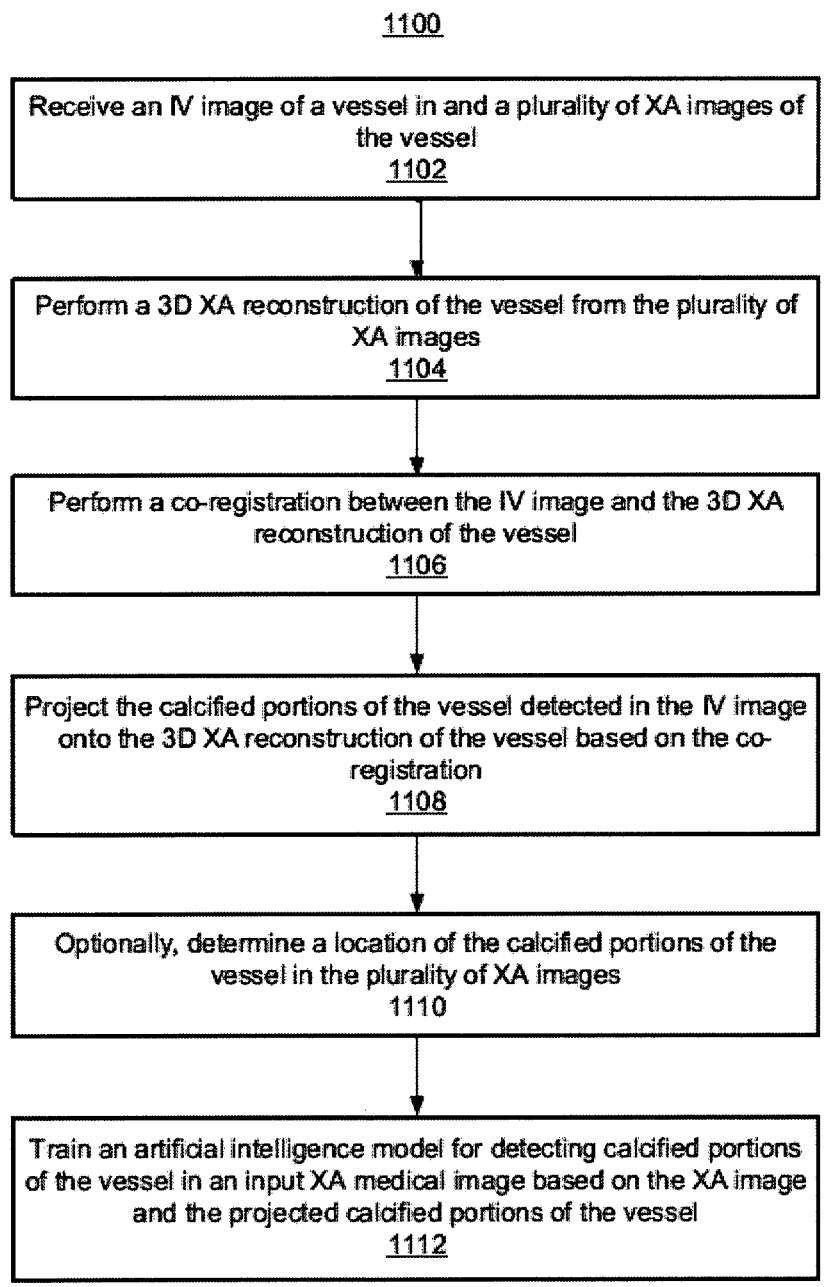
FIG. 11 shows method for training an artificial intelligence model for detecting calcified portions of a vessel in an input x-ray angiography medical image based on an intravascular image and a plurality of x-ray angiography image of a same patient.
Figure 12:
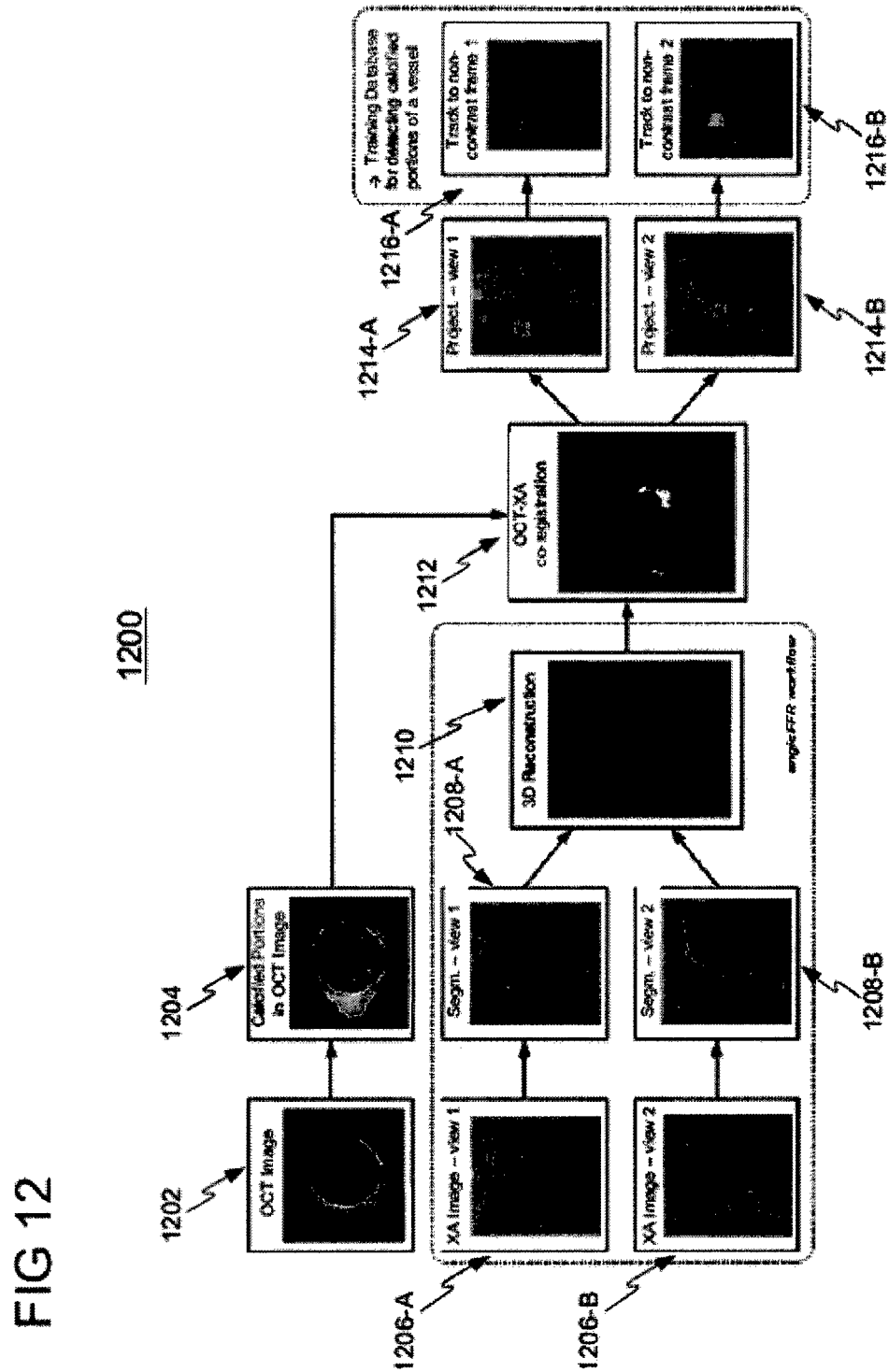
FIG. 12 shows a workflow for training an artificial intelligence model for detecting calcified portions of a vessel in an input x-ray angiography medical image based on an intravascular image and a plurality of x-ray angiography image of a same patient.

FIG. 11 shows a method 1100 for training an artificial intelligence model for detecting calcified portions of a vessel in an input XA medical image based on an IV image and a plurality of XA images of a same patient, in accordance with one or more embodiments. Steps of method 1100 may be performed by any suitable computing device, such as, e.g., computer 1402 of FIG. 14, unless otherwise noted. In one embodiment, the steps of method 1100 are performed at block 306 of workflow 300 in FIG. 3 where the IV image corresponds to the first medical image in the first modality and the plurality of XA images corresponds to the second medical image in the second modality. It should be understood that while method 1100 is described with respect to an IV image and a plurality of XA images, the images may be of any suitable modality. Method 1100 will be simultaneously described with reference to FIG. 12, which shows a workflow 1200 for training an artificial intelligence model for detecting calcified portions of a vessel in an input XA medical image based on an IV image and a plurality of XA image of a same patient, in accordance with one or more embodiments.

At step 1102, an IV image of a vessel (e.g., coronary artery) and a plurality of XA images of the vessel are received. The IV image and the plurality of XA images are of a same vessel of a same patient. Workflow 1200 shows an OCT image 1202 (i.e., an IV image) and XA image view 1 1206-A and view 2 1206-B. OCT image 1204 shows OCT image 1202 with detected calcified portions of the vessel (e.g., detected at step 304 of FIG. 3).

At step 1104, a 3D XA reconstruction of the vessel is performed from the plurality of XA images. The 3D XA reconstruction of the vessel may be performed using any suitable (e.g., known) approach. In workflow 1200, the vessel is segmented from OCT images 1206-A and 1206-B to provide segmentations 1208-A and 1208-B, respective. Segmentations 1208-A and 1208-B are used to generate the 3D XA reconstruction of the vessel.

At step 1106, a co-registration is performed between the IV image and the 3D XA reconstruction of the vessel. Workflow 1200 shows co-registration 1212 of the OCT image 1204 (with the detected calcified portions of the vessel) and the 3D XA reconstruction. The co-registration spatially aligns features of the IV image and the 3D XA reconstruction of the vessel to generate a composite image that defines a correspondence between pixels/voxels in the IV image and the 3D XA reconstruction (and therefore the plurality of XA images). The co-registration is performed based on clearly identifiable landmarks (e.g., bifurcations, etc.) and other information (e.g., radius). The co-registration may be performed using any suitable approach. In one embodiment, the co-registration is manually performed.

At step 1108, calcified portions of the vessel detected in the IV image (e.g., detected at step 304 of FIG. 3) are projected onto the plurality of XA images based on the co-registration. Workflow 1200 shows XA images 1214-A and 1214-B with projected calcified portions of the vessel projected thereon, generated by projecting the calcified portions onto XA images 1206-A and 1206-B based on co-registration 1212. In particular, the pixels in the XA images that correspond to the pixels depicting the calcified portions of the vessel in the IV image are determined based on the co-registration (e.g., the composite image resulting from the co-registration). The projected calcified portions of the vessel in the XA image may be represented by one or more bounding boxes, segmentations, labeled or highlighted pixels in the XA image, or any other suitable form.

At step 1110, a location of the calcified portions of the vessel in other XA frames is optionally determined. The other XA frames are other frames of the angiography corresponding to different points in time. Framework 1200 shows the location of the calcified portions of the vessel tracked to non-contrast frames 1216-A and 1216-B. In one embodiment, the location of the calcified portions of the vessel in other XA frames is determined using a tracking algorithm. Other approaches are also contemplated.

At step 1112, an artificial intelligence model is trained for detecting calcified portions of the vessel in an input XA medical image based on the plurality of XA images and the projected calcified portions of the vessel on the plurality of XA images. The input XA medical image may be a single XA frame or a series of consecutive or non-consecutive frames. In one embodiment, the artificial intelligence model may also be trained based on the location of the calcified portions of the vessel in other XA frames (optionally performed at step 1110). The artificial intelligence model may be any suitable artificial intelligence model, such as, e.g., a machine learning model. It should be understood that the steps of method 1100 may be performed for any number of pairs of IV and XA images (each of a same respective patient) to train the artificial intelligence model.

Various additional embodiments of the invention will now be discussed.

In accordance with one embodiment, a method for detecting and updating calcified portions of a vessel during an intervention (e.g., during an angiography while the images are being acquired) is described. A first XA image of an angiography of a vessel is acquired and calcified portions of the vessel in the first XA image are detected and/or assessed, e.g., according to method 300 of FIG. 3. A next XA image of the angiography of the vessel is then acquired and calcified portions of the vessel in the next XA image are detected and/or assessed, e.g., according to method 300 of FIG. 3. A co-registration is performed to align spatial features of all XA images of the angiography (initially, the first XA image and the next XA image). The detected calcified portions of the vessel are updated on all XA images of the angiography based on the co-registration. Due to vessel overlap, different acquisition angles, etc., the detected calcified portions of the vessel may not be equally well visible on all of the XA images of the angiography. The information from the XA images may be merged based on union techniques, intersection techniques, or any other suitable technique. The method may continue for any number of next XA images of the vessel by repeatedly acquiring a next XA image, detecting and/or assessing calcified portions in the next XA image, performing a co-registration on all the XA images of the angiography, and updating the detected calcified portions on all XA images of the angiography based on the co-registration.

In accordance with one embodiment, the detection of calcified portions of a vessel in an XA image may be fine-tuned based on an IV image. One or more XA images of an angiography of a vessel are acquired and one or more IV images are acquired (simultaneous with the acquisition of the XA images) for the vessel. A co-registration is performed to spatially align features of the XA images and the IV images. Calcified portions of the vessel are detected in the XA images and the IV images, e.g., according to method 300 of FIG. 3. Since the calcified portions of the vessel are generally more reliably detected in the IV images, the detected calcified portions of the vessel in the IV images are used as ground truths to fine-tune the detection of the calcified portions of the vessel in the XA images. For example, detecting the calcified portions of the vessel in the XA images may involve a post-processing step, such as, e.g., thresholding or other post-processing techniques to tune parameters to obtain an optimal result. In this embodiment, only the XA images simultaneously acquired with the IV may be used, or all acquired XA images may be used. One advantage of this embodiment is that while IV images may be acquired for a single vessel (e.g., single segments), the detected calcified portions of the vessel may be optimized or improved for all vessels visible in the XA images.

Figure 13:
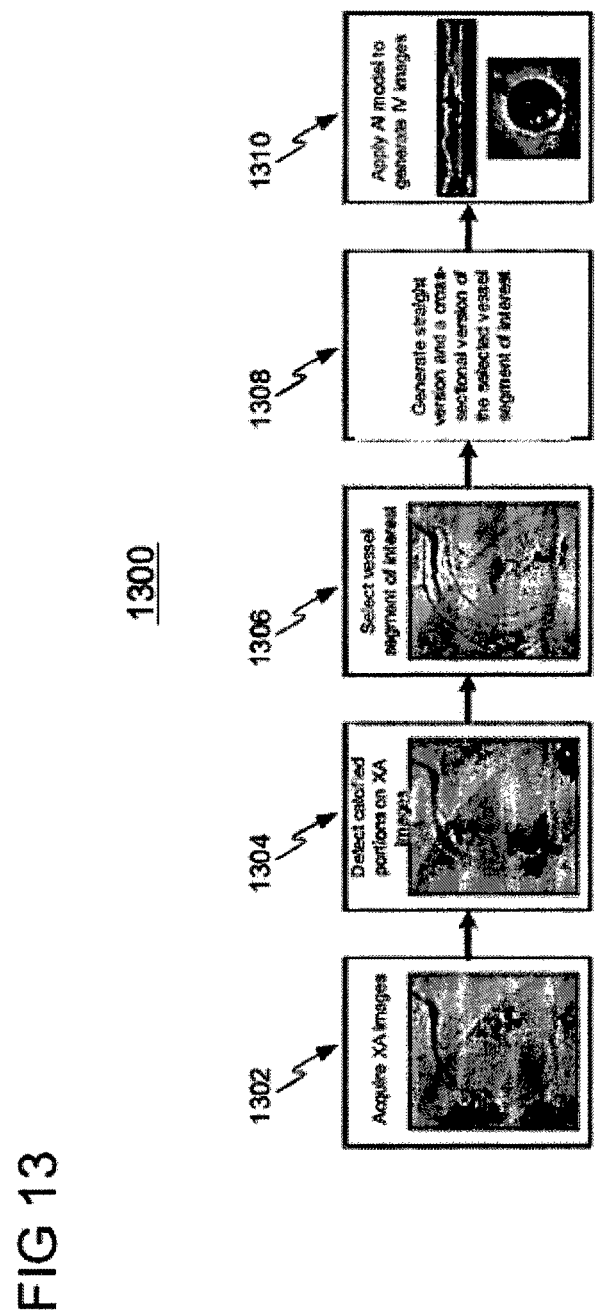
FIG. 13 shows a workflow for generating intravascular images from x-ray angiography images.

In accordance with one embodiment, XA images, on which calcified portions have been detected, may be used to generate corresponding IV images. FIG. 13 shows a workflow 1300 for generating IV images from XA images, in accordance with one or more embodiment. At step 1302, one or more XA images of an angiography of a vessel are acquired. At step 1304 calcified portions of the vessel in the XA images are detected, e.g., according to method 300 of FIG. 3. At step 1306, a vessel segment of interest is selected for the XA images. At step 1308, a straight version and a cross-sectional version of the selected vessel segment are generated with angiographic appearances. The cross-sectional version of the selected vessel segment may be generated, e.g., based on the assumption of a circular or elliptical lumen cross-section. At step 1310, a trained artificial intelligence model (e.g., a GAN) is applied to generate IV images of the straight version and the cross-sectional version of the selected vessel segment.

In accordance with one embodiment, clinical decision making may be aided based on a prior CCTA exam. In non-acute cases (e.g., stable CAD patients) and low risk acute cases (e.g., Non-ST-elevation myocardial infarction or unstable angina CAD patients), a CCTA exam may be performed prior to the intervention (e.g., angiography). Since calcified portions of a vessel are particularly well visible on CCTA images, the CCTA images may be used to aid clinical decision making during the intervention. First, a CCTA exam is performed and multiple 2D projections are generated from the CCTA exam (e.g., using standard angiographic acquisition angles). An artificial intelligence model is employed to generate XA images from the CCTA based 2D projections. Calcified portions of the vessel are highlighted on the XA images (based on the calcified portions of the vessel detected in the CCTA images during the CCTA exam) and visualized by the clinician prior to the intervention. Optionally, XA images acquired during the intervention may be used to fine-tune all pre-computed projections.

In accordance with one embodiment, uncertainty in the quantification of calcification may be estimated. During a training stage for training an artificial intelligence model for detecting calcified portions of a vessel in XA images, ground truth location and extension of the calcified portions may be provided by images acquired of different modalities (e.g., CCTA or IV images) which provide better sensitivity and specificity to the identification of the calcified portions of the vessel. While the artificial intelligence model is trained to minimize discrepancies between the ground truth and the detected values (e.g., location and extension of calcification) on the XA images, the inference errors can be analyzed to define a measure of uncertainty. For example, errors in the identification of the location of the calcified portions, as evaluated on a training set or on a validation set, can be analyzed as a function of a target vessel (quantification of calcification for more distal vessels is expected to be more challenging due to their smaller diameter), but also based on the image style (angiography with different s-ray intensity, frame rate, spatial resolution, etc.). Based on the estimated uncertainty, the artificial intelligence model can be trained to recommend the acquisition of additional data (e.g., XA images or IV images) to increase confidence in the estimation.

In one embodiment, the uncertainty in the quantification of calcification may be determined by acquiring an XA image and detecting calcified portions in the XA image (e.g., according to method 300 of FIG. 3). A measure of uncertainty in the estimated amount of calcification is determined for the XA image. Based on the amount of uncertainty, the artificial intelligence model may recommend acquisition of additional input (e.g., additional XA images or IV images), or may provide an assessment (e.g., location and extension of calcification) together with a metric of confidence in the predicted assessment.

The uncertainty may be caused by various factors. For example, the training set for the artificial intelligence model to determine the calcified portions of the vessel may be generated by projecting ground truth calcified portions in, e.g., IV or CCTA images onto XA images. However, the generated or synthesized XA images with projected ground truth calcified portions may not allow for a precise characterization of the calcification (due to, e.g., the simulated angulation of the C-arm not allowing proper visualization of the vessel segment with the calcified portions, or noise present or intrinsic to the image synthesis process). Therefore, detection and quantification of the calcified portions may be affected by an error which is a function of, e.g., a position of the calcified portions in the vessel and angulation of the simulated x-ray detector. The error may be computed, e.g., as a difference between the ground truth location and extension of the calcification and the detected value. Accordingly, for each detection result, a measure of uncertainty may be defined as a percent error of the characteristics of the detected calcification, normalized over the ground truth values. A dedicated artificial intelligence model can be trained to predict uncertainty in the detection of the calcified portions, given the XA image as input (and possibly inputs, such as, e.g., x-ray angulation). The dedicated artificial intelligence model computes uncertainty in real time and provides it as feedback to the clinician.

Embodiments described herein may classify calcified portions of a vessel, e.g., as moderate or severe. Artificial intelligence models trained to classify calcified portions of a vessel may be trained based on, e.g., outcome data of interventions (e.g., cases in which stent deployment was sub-optimal due to severe calcification).

Embodiments described herein may use an image-to-image approach or a patch-wise approach, e.g., to perform the detection of the calcified portions only in the proximity of a target vessel (e.g., the coronary lumen, which may be detected using, e.g., an artificial intelligence based vesselness model).

Embodiments described herein input an XA image as, e.g., a single XA frame or a sequence of consecutive or non-consecutive XA frames.

Embodiments described herein may train an additional artificial intelligence model to provide a recommendation on an optimal treatment strategy based on the detected calcified portions (e.g., a location and extent of calcification) and the calcification score.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2, 3, 5-8, and 10-13. Certain steps or functions of the methods and workflows described herein, including one or more of the steps or functions of FIGS. 2, 3, 5-8, and 10-13, may be performed by a server or by another processor in a network-based cloud-computing system. Certain steps or functions of the methods and workflows described herein, including one or more of the steps of FIGS. 2, 3, 5-8, and 10-13, may be performed by a client computer in a network-based cloud computing system. The steps or functions of the methods and workflows described herein, including one or more of the steps of FIGS. 2, 3, 5-8, and 10-13, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2, 3, 5-8, and 10-13, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 14:
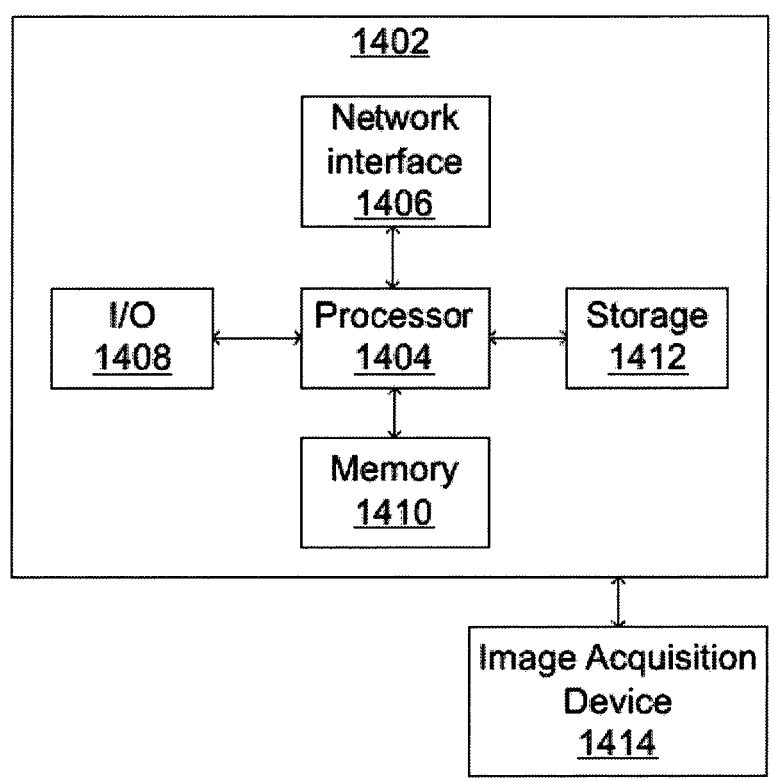
FIG. 14 shows a high-level block diagram of a computer.

A high-level block diagram of an example computer 1402 that may be used to implement systems, apparatus, and methods described herein is depicted in FIG. 14. Computer 1402 includes a processor 1404 operatively coupled to a data storage device 1412 and a memory 1410. Processor 1404 controls the overall operation of computer 1402 by executing computer program instructions that define such operations. The computer program instructions may be stored in data storage device 1412, or other computer readable medium, and loaded into memory 1410 when execution of the computer program instructions is desired. Thus, the method and workflow steps or functions of FIGS. 2, 3, 5-8, and 10-13 can be defined by the computer program instructions stored in memory 1410 and/or data storage device 1412 and controlled by processor 1404 executing the computer program instructions. For example, the computer program instructions can be implemented as computer executable code programmed by one skilled in the art to perform the method and workflow steps or functions of FIGS. 2, 3, 5-8, and 10-13. Accordingly, by executing the computer program instructions, the processor 1404 executes the method and workflow steps or functions of FIGS. 2, 3, 5-8, and 10-13. Computer 1402 may also include one or more network interfaces 1406 for communicating with other devices via a network. Computer 1402 may also include one or more input/output devices 1408 that enable user interaction with computer 1402 (e.g., display, keyboard, mouse, speakers, buttons, etc.).

Processor 1404 may include both general and special purpose microprocessors, and may be the sole processor or one of multiple processors of computer 1402. Processor 1404 may include one or more central processing units (CPUs), for example. Processor 1404, data storage device 1412, and/or memory 1410 may include, be supplemented by, or incorporated in, one or more application-specific integrated circuits (ASICs) and/or one or more field programmable gate arrays (FPGAs).

Data storage device 1412 and memory 1410 each include a tangible non-transitory computer readable storage medium. Data storage device 1412, and memory 1410, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1408 may include peripherals, such as a printer, scanner, display screen, etc. For example, input/output devices 1408 may include a display device such as a cathode ray tube (CRT) or liquid crystal display (LCD) monitor for displaying information to the user, a keyboard, and a pointing device such as a mouse or a trackball by which the user can provide input to computer 1402.

An image acquisition device 1414 can be connected to the computer 1402 to input image data (e.g., medical images) to the computer 1402. It is possible to implement the image acquisition device 1414 and the computer 1402 as one device. It is also possible that the image acquisition device 1414 and the computer 1402 communicate wirelessly through a network. In a possible embodiment, the computer 1402 can be located remotely with respect to the image acquisition device 1414.

Any or all of the systems and apparatus discussed herein may be implemented using one or more computers such as computer 1402.

One skilled in the art will recognize that an implementation of an actual computer or computer system may have other structures and may contain other components as well, and that FIG. 14 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method, comprising:
   receiving one or more first medical images of a vessel in a first modality and one or more second medical images of the vessel in a second modality;
   detecting calcified portions of the vessel in the one or more first medical images; and
   training an artificial intelligence model for detecting calcified portions of a vessel in an input medical image in the second modality based on the one or more second medical images and the calcified portions of the vessel detected in the one or more first medical images.

2. The method of claim 1, wherein training an artificial intelligence model for detecting calcified portions of a vessel in an input medical image in the second modality based on the one or more second medical images and the calcified portions of the vessel detected in the one or more first medical images comprises:
   performing a co-registration between the one or more first medical images and the one or more second medical images;
   projecting the calcified portions detected in the one or more first medical images onto the one or more second medical images based on the co-registration; and
   training the artificial intelligence model based on the projected calcified portions of the vessel.

3. The method of claim 2, wherein the first modality is computed tomography, the second modality is x-ray angiography, and the one or more first medical images and the one or more second medical images are of a same patient.

4. The method of claim 1, wherein training an artificial intelligence model for detecting calcified portions of a vessel in an input medical image in the second modality based on the one or more second medical images and the calcified portions of the vessel detected in the one or more first medical images comprises:
   generating one or more synthesized medical images of the vessel in the second modality based on the one or more first medical images using another artificial intelligence model; and
   training the artificial intelligence model based on the one or more synthesized medical images of the vessel.

5. The method of claim 4, wherein generating one or more synthesized medical images of the vessel in the second modality based on the one or more first medical images using another artificial intelligence model comprises:
   generating the one or more synthesized medical images each corresponding to different acquisition angles.

6. The method of claim 4, further comprising training the other artificial intelligence model by:
   grouping the one or more second medical images based on their acquisition angles;

computing a two-dimensional projection of the one or more first medical images for each of the acquisition angles; and training the other artificial intelligence model based on the two-dimensional projection of the one or more first medical images for each of the acquisition angles and the grouped one or more second medical images.

7. The method of claim 4, wherein the first modality is computed tomography, the second modality is x-ray angiography, and the one or more first medical images and the one or more second medical images are of different patients.

8. The method of claim 1, wherein training an artificial intelligence model for detecting calcified portions of a vessel in an input medical image in the second modality based on the one or more second medical images and the calcified portions of the vessel detected in the one or more first medical images comprises:

computing longitudinal projections of the one or more first medical images for a plurality of angles;

mapping the computed longitudinal projections of the one or more first medical images to a two-dimensional vessel tree;

generating one or more synthesized medical images of the vessel in the second modality based on the two-dimensional vessel tree using another artificial intelligence model; and training the artificial intelligence model based on the one or more synthesized medical images.

9. The method of claim 8, wherein generating one or more synthesized medical images of the vessel in the second modality based on the two-dimensional vessel tree comprises:

generating the one or more synthesized medical images each corresponding to one of the plurality of angles.

10. The method of claim 8, further comprising training the other artificial intelligence model by:

computing a longitudinal projection of the one or more first medical images for each of the plurality of angles;

mapping the computed longitudinal projections to a particular two-dimensional vessel tree; and training the artificial intelligence model based on the particular two-dimensional vessel tree.

11. The method of claim 8, wherein the first modality is an intravascular imaging modality, the second modality is x-ray angiography, and the one or more first medical images and the one or more second medical images are of different patients.

12. The method of claim 1, wherein training an artificial intelligence model for detecting calcified portions of a vessel in an input medical image in the second modality based on the one or more second medical images and the calcified portions of the vessel detected in the one or more first medical images comprises:

performing a three-dimensional reconstruction of the vessel from the one or more second medical images;

performing a co-registration between the one or more first medical images and the three-dimensional reconstruction of the vessel;

projecting the calcified portions of the vessel detected in the one or more first medical images onto the three-dimensional reconstructions based on the co-registration; and training the artificial intelligence model based on the projected calcified portions of the vessel.

13. The method of claim 12, wherein the first modality is an intravascular imaging modality, the second modality is x-ray angiography, and the one or more first medical images and the one or more second medical images are of a same patient.

14. The method of claim 1, further comprising:

receiving the input medical image in the second modality;

detecting the calcified portions of the vessel in the input medical image using the trained artificial intelligence model; and determine a calcification score quantifying calcification in one or more of the calcified portions of the vessel detected in the input medical image.

15. An apparatus, comprising:

means for receiving one or more first medical images of a vessel in a first modality and one or more second medical image of the vessel in a second modality;

means for detecting calcified portions of the vessel in the one or more first medical images; and means for training an artificial intelligence model for detecting calcified portions of a vessel in an input medical image in the second modality based on the one or more second medical images and the calcified portions of the vessel detected in the one or more first medical images.

16. The apparatus of claim 15, wherein the means for training an artificial intelligence model for detecting calcified portions of a vessel in an input medical image in the second modality based on the one or more second medical images and the calcified portions of the vessel detected in the one or more first medical images comprises:

means for performing a co-registration between the one or more first medical images and the one or more second medical images;

means for projecting the calcified portions detected in the one or more first medical images onto the one or more second medical images based on the co-registration; and means for training the artificial intelligence model based on the projected calcified portions of the vessel.

17. The apparatus of claim 15, wherein the means for training an artificial intelligence model for detecting calcified portions of a vessel in an input medical image in the second modality based on the one or more second medical images and the calcified portions of the vessel detected in the one or more first medical images comprises:

means for generating one or more synthesized medical images of the vessel in the second modality based on the one or more first medical images using another artificial intelligence model; and means for training the artificial intelligence model based on the one or more synthesized medical images of the vessel.

18. A non-transitory computer readable medium storing computer program instructions, the computer program instructions when executed by a processor cause the processor to perform operations comprising:

receiving one or more first medical images of a vessel in a first modality and one or more second medical image of the vessel in a second modality;

detecting calcified portions of the vessel in the one or more first medical images; and training an artificial intelligence model for detecting calcified portions of a vessel in an input medical image in the second modality based on the one or more second medical images and the calcified portions of the vessel detected in the one or more first medical images.

19. The non-transitory computer readable medium of claim 18, wherein training an artificial intelligence model for detecting calcified portions of a vessel in an input medical image in the second modality based on the one or more second medical images and the calcified portions of the vessel detected in the one or more first medical images comprises:
- computing longitudinal projections of the one or more first medical images for a plurality of angles;
- mapping the computed longitudinal projections of the one or more first medical images to a two-dimensional vessel tree;
- generating one or more synthesized medical images of the vessel in the second modality based on the two-dimensional vessel tree using another artificial intelligence model; and
- training the artificial intelligence model based on the one or more synthesized medical images.

20. The non-transitory computer readable medium of claim 18, wherein training an artificial intelligence model for detecting calcified portions of a vessel in an input medical image in the second modality based on the one or more second medical images and the calcified portions of the vessel detected in the one or more first medical images comprises:
- performing a three-dimensional reconstruction of the vessel from the one or more second medical images;
- performing a co-registration between the one or more first medical images and the three-dimensional reconstruction of the vessel;
- projecting the calcified portions of the vessel detected in the one or more first medical images onto the three-dimensional reconstructions based on the co-registration; and
- training the artificial intelligence model based on the projected calcified portions of the vessel.

* * * * *